United States Patent [19]

Smith

[11] 4,140,721

[45] Feb. 20, 1979

[54] 2-DECARBOXY-2-HYDROXYMETHYL-13,14-DIDEHYDRO-17-PHENYL-PGA, PGD AND PGE COMPOUNDS

[75] Inventor: Herman W. Smith, Kalamazoo, Mich.

[73] Assignee: The Upjohn Company, Kalamazoo, Mich.

[21] Appl. No.: 880,741

[22] Filed: Feb. 24, 1978

Related U.S. Application Data

[62] Division of Ser. No. 814,410, Jul. 11, 1977, which is a division of Ser. No. 708,752, Jul. 26, 1976, Pat. No. 4,058,564.

[51] Int. Cl.² .................................................. C07C 49/78
[52] U.S. Cl. .................................................. 260/590 C
[58] Field of Search ...................................... 260/590 C

[56] References Cited

U.S. PATENT DOCUMENTS

| | | | |
|---|---|---|---|
| 3,935,254 | 1/1976 | Gandolfe et al. | 260/594 D |
| 3,984,400 | 10/1976 | Eggler et al. | 260/468 D |

*Primary Examiner*—Jaems O. Thomas, Jr.
*Assistant Examiner*—James H. Reamer
*Attorney, Agent, or Firm*—Robert A. Armitage

[57] ABSTRACT

This invention comprises certain analogs of the prostaglandins in which the C-1 carboxyl is replaced by a primary alcohol and the double bond between C-13 and C-14 is replaced by a triple bond. Also provided in this invention, are novel chemical processes useful in the preparation of the above prostaglandin analogs. These prostanglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

74 Claims, No Drawings

2-DECARBOXY-2-HYDROXYMETHYL-13,14-DIDEHYDRO-17-PHENYL-PGA, PGD AND PGE COMPOUNDS

The present application is a divisional application of Ser. No. 814,410, filed July 11, 1977, now pending, which application is a divisional application of Ser. No. 708,752, filed July 26, 1976, issued as U.S. Pat. No. 4,058,564 on Nov. 15, 1977.

The present invention relates to prostaglandin analogs for which the essential material constituting a disclosure therefor is incorporated by reference here from U.S. Pat. No. 4,058,564, issued Nov. 15, 1977.

I claim:

1. A prostaglandin analog of the formula

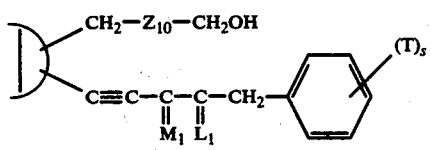

wherein

D is

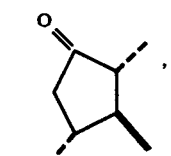

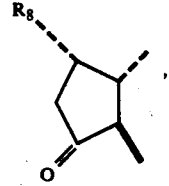

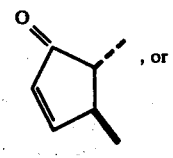, or

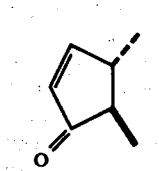

wherein $R_8$ is hydrogen or hydroxy;
wherein $M_1$ is

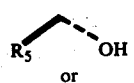
or

wherein $R_5$ is hydrogen or methyl;
wherein $L_1$ is

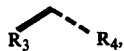

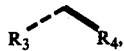

or a mixture of

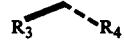
and

wherein $R_3$ and $R_4$ are hydrogen, methyl, or fluoro, being the same or different, with the proviso that one of $R_3$ and $R_4$ is methyl only when the other is hydrogen or methyl;

wherein $Z_{10}$ is
(1) cis—CH=CH—CH—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$-CH$_2$—,
(4) —(CH$_2$)$_3$—(CH$_2$)$_g$—CH$_2$—,
(5) —(CH$_2$)$_3$—(CH$_2$)$_g$—CF$_2$—, or
(6) —CH$_2$—O—CH$_2$—(CH$_2$)$_g$—CH$_2$—, wherein g is one, 2, or 3; and wherein s is one to 3, inclusive and T is chloro, fluoro, trifluoromethyl, alkyl of one to 3 carbon atoms, inclusive, or alkoxy of one to 3 carbon atoms, inclusive, the various T's being the same or different, with the proviso that not more than two are other than alkyl.

2. A prostaglandin analog according to claim 1, wherein D is

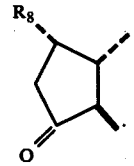

3. A prostaglandin analog according to claim 2, wherein $R_8$ is hydrogen.

4. A prostaglandin analog according to claim 2, wherein $R_8$ is hydroxy.

5. A prostaglandin analog according to claim 1, wherein D is

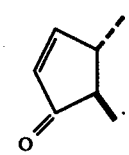

6. A prostaglandin analog according to claim 1, wherein D is

7. A prostaglandin analog according to claim 1, wherein D is

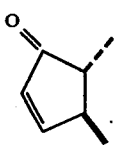

8. A prostaglandin analog according to claim 7, wherein $Z_{10}$ is cis—CH=CH—CH$_2$—(CH$_2$)$_g$—CF$_2$—.

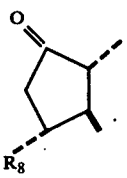

9. 2-Decarboxy-2-hydroxymethyl-2,2-difluoro-13,14-didehydro-17-phenyl-18,19,20-trinor-PGE$_2$, a prostaglandin analog according to claim 8.

10. A prostaglandin analog to claim 7, wherein $Z_{10}$ is —(CH$_2$)$_3$—(CH$_2$)g—CF$_2$—.

11. 2-Decarboxy-2-hydroxymethyl-2,2-difluoro-13,14-didehydro-17-phenyl-18,19,20-trinor-PGE$_1$, a prostglandin analog according to claim 10.

12. A prostaglandin analog according to claim 7, wherein $Z_{10}$ is cis—CH$_2$—CH=CH—(CH$_2$)$_g$—CH$_2$—.

13. 2-Decarboxy-2-hydroxymethyl-cis-4,5didehydro-13,14-didehydro-17-phenyl 18,19,20-trinor-PGE$_1$, a prostaglandin according to claim 12.

14. A prostaglandin analog according to claim 7, wherein $Z_{10}$ is —CH$_2$—O—CH$_2$—(CH$_2$)$_g$—CH$_2$—.

15. 2-Decarboxy-2-hydroxymethyl-5-oxa-13,14-didehydro-17-phenyl-18,19,20-trinor-PGE$_1$, a prostglandin analog according to claim 14.

16. A prostaglandin analog according to claim 7, wherein $Z_{10}$ is —(CH$_2$)$_3$—(CH$_2$)$_g$—CH$_2$—.

17. A prostaglandin analog according to claim 16, wherein $M_1$ is

18. 2-Decarboxy-2-hydroxymethyl-15-epi-13,14-didehydro-17-phenyl-18,19,20-trinor-PGE$_1$, a prostaglandin analog according to claim 17.

19. A prostaglandin analog according to claim 16, wherein $M_1$ is

20. A prostaglandin analog according to claim 19, wherein m is 3.

21. A prostaglandin analog according to claim 20, wherein g is 3.

22. 2-Decarboxy-2-hydroxymethyl-2a,2b-dihomo-15-methyl-13,14-didehydro-17-phenyl-18,19,20-trinor-PGE$_1$, a prostaglandin analog according to claim 21.

23. 2-Decarboxy-2-hydroxymethyl-2a,2b-dihomo-13,14-didehydro-17-phenyl-18,19,20-trinor-PGE$_1$, a prostaglandin analog according to claim 21.

24. A prostaglandin analog according to claim 20, wherein g is 1.

25. A prostaglandin analog according to claim 24, wherein at least one of $R_3$ and $R_4$ is methyl.

26. A prostaglandin analog according to claim 25, wherein $R_3$ and $R_4$ are both methyl.

27. 2-Decarboxy-2-hydroxymethyl-13,14-didehydro-16,16-dimethyl-17-phenyl-18,19,20-trinor-PGE$_1$, a prostaglandin analog according to claim 26.

28. A prostaglandin analog according to claim 27, wherein at least two of $R_3$, $R_4$, and $R_5$ are methyl.

29. A prostaglandin analog according to claim 28, wherein $R_3$, $R_4$, and $R_5$ are all methyl.

30. 2-Decarboxy-2-hydroxymethyl-15,16,16-trimethyl-13,14-didehydro-17-phenyl-18,19,20-trinor-PGE$_1$, a prostaglandin analog according to claim 29.

31. A prostaglandin analog according to claim 24, wherein $R_3$ and $R_4$ are both hydrogen.

32. A prostaglandin analog according to claim 31, wherein $R_5$ is methyl.

33. 2-Decarboxy-2-hydroxymethyl-15-methyl-13,14-didehydro-17-phenyl-18,19,20-trinor-PGE$_1$, a prostaglandin analog according to claim 31.

34. A prostaglandin analog according to claim 31, wherein $R_5$ is hydrogen.

35. 2-Decarboxy-2-hydroxymethyl-13,14-didehydro-17-phenyl-18,19,20-trinor-PGE$_1$, a prostaglandin analog according to claim 34.

36. A prostaglandin analog according to claim 7, wherein $Z_{10}$ is cis—CH=CH—CH$_2$—(CH$_2$)$_g$—CH$_2$—.

37. A prostaglandin analog according to claim 36, wherein $M_1$ is

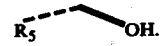

38. A prostaglandin analog according to claim 37, wherein m is 3.

39. A prostaglandin analog according to claim 38, wherein g is 3.

40. 2-Decarboxy-2-hydroxymethyl-2a,2b-dihomo-15-epi-15-methyl-13,14-didehydro-17-phenyl-18,19,20-trinor-PGE$_2$, a prostaglandin analog according to claim 39.

41. 2-Decarboxy-2-hydroxymethyl-2a,2b-dihomo-15-epi-13,14-didehydro-17-phenyl-18,19,20-trinor-PGE$_2$, a prostaglandin analog according to claim 39.

42. A prostaglandin analog according to claim 38, wherein g is 1.

43. A prostaglandin analog according to claim 42, wherein at least one of $R_3$ and $R_4$ is methyl.

44. 2-Decarboxy-2-hydroxymethyl-15-epi-13,14-didehydro-16,16-dimethyl-17-phenyl-18,19,20-trinor-PGE$_2$, a prostaglandin analog according to claim 43.

45. A prostaglandin analog according to claim 42, wherein at least two of $R_3$, $R_4$, and $R_5$ are methyl.

46. 2-Decarboxy-2-hydroxymethyl-15-epi-15,16,16-trimethyl-13,14-didehydro-17-phenyl-18,19,20-trinor-PGE$_2$, a prostaglandin analog according to claim 40.

47. A prostaglandin analog according to claim 42, wherein $R_3$ and $R_4$ are both hydrogen.

48. 2-Decarboxy-2-hydroxymethyl-15-epi-15-methyl-13,14-didehydro-17-phenyl-18,19,20-trinor-PGE$_2$, a prostaglandin analog according to claim 47.

49. A prostaglandin analog according to claim 36, wherein $M_1$ is

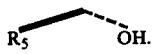

50. A prostaglandin analog according to claim 49, wherein m is 3.

51. A prostaglandin analog according to claim 50, wherein g is 3.

52. A prostaglandin analog according to claim 51, wherein at least one of $R_3$ and $R_4$ is methyl.

53. 2-Decarboxy-2-hydroxymethyl-2a,2b-dihomo-16,16-dimethyl-13,14-didehydro-17-phenyl-18,19,20-trinor-$PGE_2$, a prostaglandin analog according to claim 52.

54. A prostaglandin analog according to claim 51, wherein at least two of $R_3$, $R_4$, and $R_5$ are methyl.

55. 2-Decarboxy-2-hydroxymethyl-2a,2b-dihomo-15,16,16-trimethyl-13,14-didehydro-17-phenyl-18,19,20-trinor-$PGE_2$, a prostaglandin analog according to claim 54.

56. A prostaglandin analog according to claim 51, wherein $R_3$ and $R_4$ are both hydrogen.

57. 2-Decarboxy-2-hydroxymethyl-2a,2b-dihomo-15-methyl-13,14-didehydro-17-phenyl-18,19,20-trinor-$PGE_2$, a prostaglandin analog according to claim 56.

58. A prostaglandin analog according to claim 50, wherein g is 1.

59. A prostaglandin analog according to claim 58, wherein at least one of $R_3$ and $R_4$ is methyl.

60. A prostaglandin analog according to claim 59, wherein only one of $R_3$ and $R_4$ is methyl.

61. 2-Decarboxy-2-hydroxymethyl-13,14-didehydro-16-methyl-17-phenyl-18,19,20-trinor-$PGE_2$, a prostaglandin analog according to claim 60.

62. A prostaglandin analog according to claim 59, wherein $R_3$ and $R_4$ are both methyl.

63. 2-Decarboxy-2-hydroxymethyl-13,14-didehydro-16,16-dimethyl-17-phenyl-18,19,20-trinor-$PGE_2$, a prostaglandin analog according to claim 62.

64. A prostaglandin analog according to claim 58, wherein at least one of $R_3$ and $R_4$ is fluoro.

65. A prostaglandin analog according to claim 64, wherein $R_3$ and $R_4$ are both fluoro.

66. A prostaglandin analog according to claim 65, wherein $R_5$ is methyl.

67. 2-Decarboxy-2-hydroxymethyl-15-methyl-16,16-difluoro-13,14-didehydro-17-phenyl-18,19,20-trinor-$PGE_2$, a prostaglandin analog according to claim 66.

68. A prostaglandin analog according to claim 65, wherein $R_5$ is hydrogen.

69. 2-Decarboxy-2-hydroxymethyl-16,16-difluoro-13,14-didehydro-17-phenyl-18,19,20-trinor-$PGE_2$, a prostaglandin analog according to claim 68.

70. A prostaglandin analog according to claim 58, wherein $R_3$ and $R_4$ are both hydrogen.

71. A prostaglandin analog according to claim 70, wherein $R_5$ is methyl.

72. 2-Decarboxy-2-hydroxymethyl-15-methyl-13,14-didehydro-17-phenyl-18,19,20-trinor-$PGE_2$, a prostaglandin analog according to claim 71.

73. A prostaglandin analog according to claim 70, wherein $R_5$ is hydrogen.

74. 2-Decarboxy-2-hydroxymethyl-13,14-didehydro-17-phenyl-18,19,20-trinor-$PGE_2$, a prostaglandin analog according to claim 73.

* * * * *

UNITED STATES PATENT OFFICE
CERTIFICATE OF CORRECTION

Patent No. 4,140,721          Dated    20 February 1979

Inventor(s)    Herman W. Smith

It is certified that error appears in the above-identified patent and that said Letters Patent are hereby corrected as shown below:

Column 2, line 29, "cis-CH=CH-CH-$(CH_2)_g$-$CH_2$-" should read -- cis-CH=CH-$CH_2$-$(CH_2)_g$-$CH_2$- --; line 36, "wherein s is one to 3," should read -- wherein s is zero to 3, --;

Column 3, lines 59-60, cancel claim 20; line 61, "according to claim 20" should read -- according to claim 19 --;

Column 4, lines 38-39, cancel claim 38; line 40, "according to claim 38" should read -- according to claim 37 --;

Column 5, lines 6-7, cancel claim 50; line 8, "according to claim 50" should read -- according to claim 49 --.

Signed and Sealed this

*Ninth* Day of *September 1980*

[SEAL]

*Attest:*

*Attesting Officer*

SIDNEY A. DIAMOND

*Commissioner of Patents and Trademarks*